United States Patent [19]

Monnier et al.

[11] Patent Number: 5,374,712
[45] Date of Patent: * Dec. 20, 1994

[54] IMIDAZOPYRIDINIUM COMPOUND AND PROCESSES FOR ISOLATING, IDENTIFYING, AND CHEMICALLY SYNTHESIZING SAME

[75] Inventors: Vincent M. Monnier, Shaker Heights; David R. Sell, Cleveland Heights, both of Ohio

[73] Assignee: Case Western Reserve University, Cleveland, Ohio

[*] Notice: The portion of the term of this patent subsequent to May 25, 2010 has been disclaimed.

[21] Appl. No.: 897,987

[22] Filed: Jun. 16, 1992

Related U.S. Application Data

[63] Continuation-in-part of Ser. No. 453,959, Dec. 20, 1989, Pat. No. 5,214,138.

[51] Int. Cl.$^5$ .................. C07H 17/02; C07H 19/04
[52] U.S. Cl. .................. 536/17.3; 536/27.13; 530/356; 530/840
[58] Field of Search .................. 536/17.3, 27.13; 530/356, 840

[56] References Cited

U.S. PATENT DOCUMENTS

| | | | |
|---|---|---|---|
| 4,994,482 | 2/1991 | Meanwell | 548/375.1 |
| 5,071,866 | 12/1991 | Meanwell | 548/254 |
| 5,128,360 | 7/1992 | Cerami et al. | 514/866 |
| 5,214,138 | 5/1993 | Monnier et al. | 536/17.3 |

*Primary Examiner*—Ronald W. Griffin
*Attorney, Agent, or Firm*—Fay, Sharpe, Beall, Fagan, Minnich & McKee

[57] ABSTRACT

The present invention is directed to a novel imidazo [4,5b] pyridinium molecule composed of a lysine and an arginine residue crosslinked with a pentose sugar. The novel imidazo [4,5b] pyridinium compound, referred to as "pentosidine", was isolated from proteineous tissue undergoing advanced glycosylation and is believed to be one of the principal products involved in the nonenzymatic browning and/or aging of proteins. Assaying for the pentosidine molecule makes it possible to assess the degree of aging of proteins in vivo as mediated by pentose induced crosslinking and modulated by disease such as diabetes and nephropathy. In addition, the pentosidine molecule may be utilized through the production of monoclonal antibodies thereto and/or the preparation of test kits, etc. for diagnostic, as well as therapeutic purposes (i.e. development of agents which inhibit the non-enzymatic browning reaction, etc.).

16 Claims, 12 Drawing Sheets

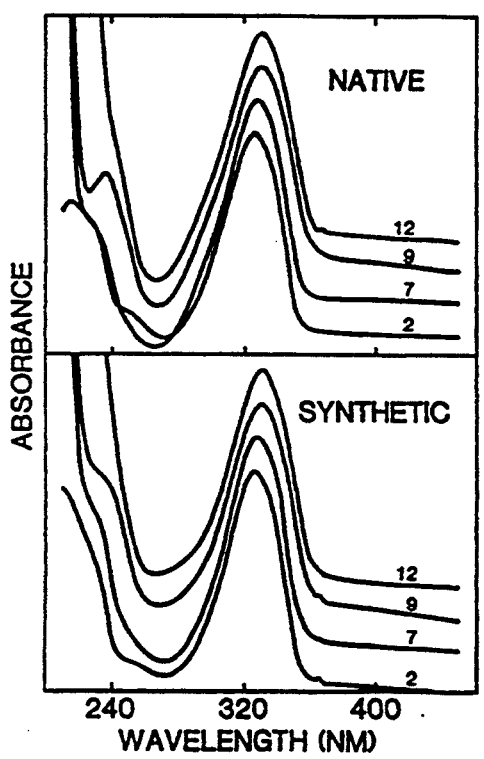 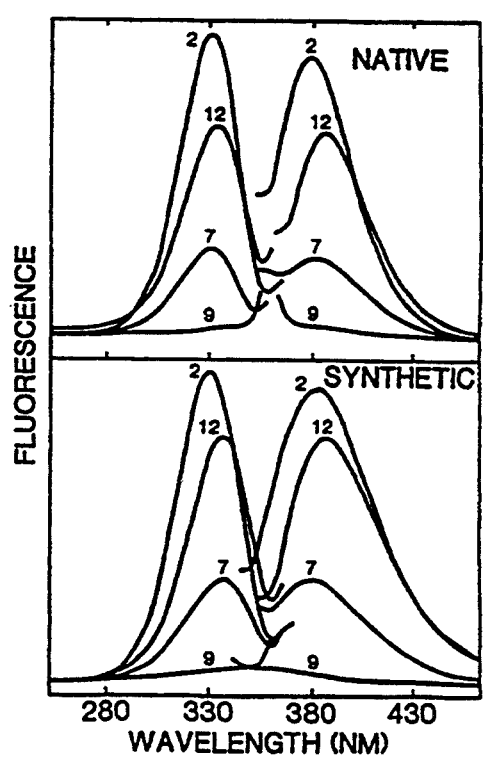
FIGURE 2A  FIGURE 2B

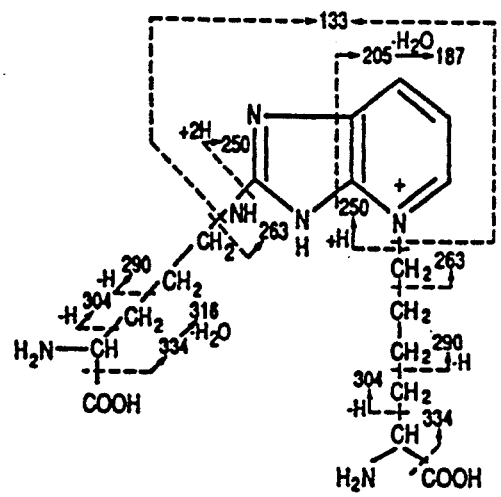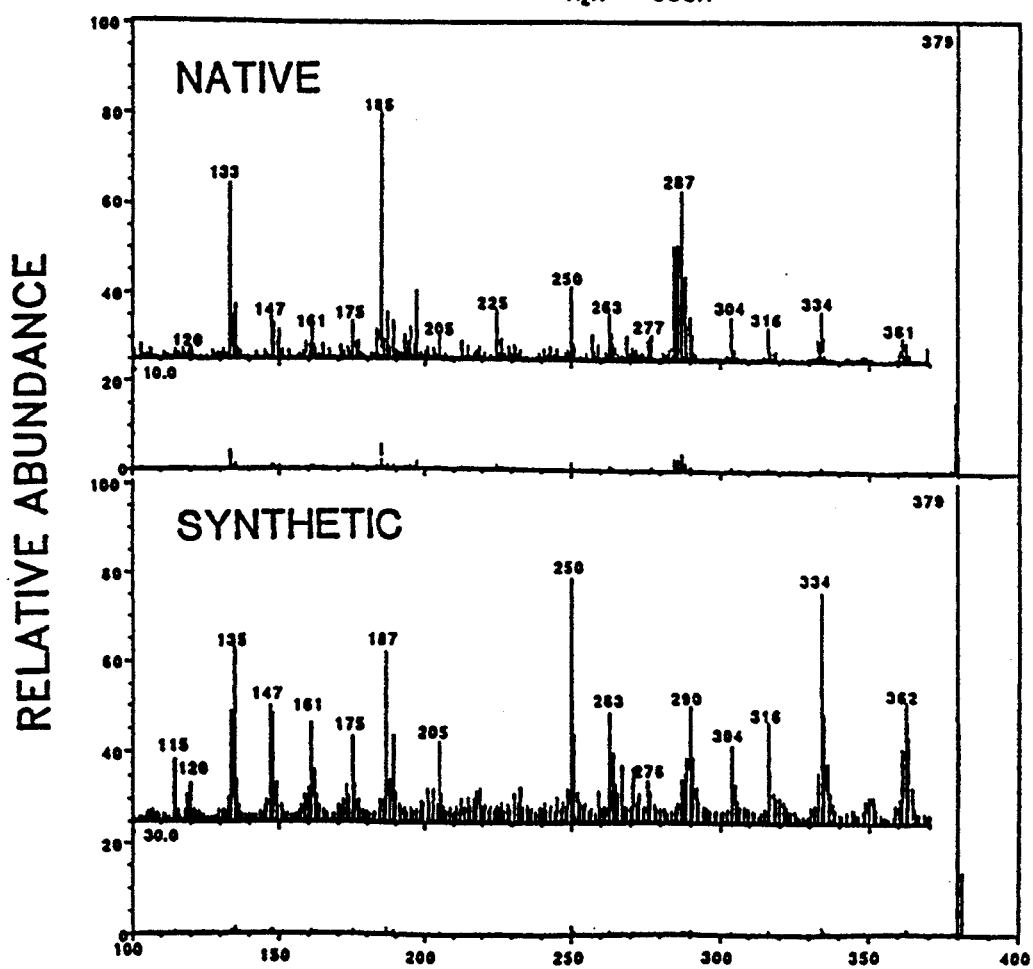
FIGURE 6

IMIDAZOPYRIDINIUM COMPOUND AND PROCESSES FOR ISOLATING, IDENTIFYING, AND CHEMICALLY SYNTHESIZING SAME

The present application is a continuation-in-part of co-pending U.S. application Ser. No. 07/453,959, filed on Dec. 20, 1989, now U.S. Pat. No. 5,214,138, issued May 25 1993.

BACKGROUND OF THE INVENTION

The present invention relates to a process for isolating and identifying a novel imidazo [4,5b] pyridinium molecule, referred to by the inventors as "pentosidine", from the extracellular matrix of humans and other mammals. The recently isolated imidazo [4,5b] pyridinium molecule, or pentosidine, is believed to be produced according to the non-enzymatic reaction of sugars with various amino acid or protein residues during the aging and/or degradation of proteins.

In this regard, the pentosidine molecule has been structurally characterized by the inventors to consist essentially of a lysine and an arginine residue crosslinked by a pentose. Furthermore, the novel imidazo [4,5b] pyridinium or pentosidine molecule of the invention has been chemically synthesized by a number of processes. Of particular interest is an improved process for synthesizing pentosidine based on the direct reaction of α-t-boc-L-deoxy ribosyl-lysine (i.e. ribated lysine) prepared from α-amino protected L-lysine and D-ribose with α-amino protected L-arginine, such as α-t-boc arginine, at a slightly alkaline pH (i.e. pH about 9) under bubbling oxygen. Under these conditions the yield of pentosidine is about 12% instead of the 0.1% previous described by the inventors.

The present invention is further directed to the use of the recently isolated, characterized, and chemically synthesized pentosidine molecule in various processes and/or compositions for studying the aging and/or degradation of proteins in humans and other mammals.

The extracellular matrix of humans and other mammals undergoes progressive changes during aging that are characterized by decreased solubility (Schnider, S. L., and Kohn, R. R., *J. Clin. Invest.* 67, pp. 1630–1635, 1981), decreased proteolytic digestibility (Hamlin, C. R., Luschin, J. H., and Kohn, R. R., *Exp. Gerontol.* 13, pp. 415–523, 1978), increased heat denaturation time (Snowden, J. M., Eyre, D. R., and Swarm, D. H., *Biochem. Biophys. Acta*, 706, pp. 153–157, 1982) and accumulation of yellow and fluorescent material (LaBella, F. S., and Paul, G., *J. Gerontol.*, 20, pp. 54–59, 1964). These changes, which affect particularly collagen-rich tissues and appear to be accelerated in diabetes, are thought to result from the formation of age-related intermolecular crosslinks.

Elucidation of the structure of these age-related intermolecular crosslinks has been for many years of major interest to gerontologists and collagen chemists for two principal reasons. First, there appears to exist an inverse relationship between mammalian longevity and aging rate of collagen (Kohn, R. R. in *Testing the Theories of Aging* (Adelman, R. C., and Roth, G. S., eds.) pp. 221–231, CRC Press, Inc., Boca Raton, Fla.) suggesting that the process which governs longevity may express itself at least partially in the aging rate of collagen. Second, the progressive increase in stiffness of collagen-rich tissues like arteries, lungs, joints and the extracellular matrix has been associated with age-related diseases such as hypertension, emphysema, decreased joint mobility and ability to fight infections. Thus, elucidation of the nature of extracellular matrix crosslinking in aging is of both practical and theoretical interest.

Along these lines, the present inventors and others previously postulated that the advanced Maillard or nonenzymatic glycosylation reaction which occurs between reducing sugars, e.g., glucose, and amino groups on proteins could explain some of the age and diabetes-related changes that affect long-lived proteins through browning and crosslinking (Monnier, V. M., and Cerami, A., *Science*, 211, pp. 491–493, 1981). However, direct demonstration of this hypothesis has not been possible since the structures of Maillard protein adducts and crosslinks were previously unknown.

In this regard, Cerami, et al., U.S. Pat. Nos. 4,665,192 and 4,758,583 reported the discovery of a new and useful fluorescent chromophore-2-(2-furoyl)-4(5)-2(furanyl)-1H-imidazole (FFI) and a method of utilizing this chromophore for inhibiting protein aging. However, the present inventors have demonstrated that the FFI compound described in these patents is an artifact of acid hydrolysis and alkalization with ammonia and is not one of the end products of extended non-enzymatic polypeptide glycosylation (Njoroge, et al., *J.Biol. Chem.*, 263: 10646–10652, 1988).

However, notwithstanding the above, recent observations continue to suggest that some of the changes occurring in the aging process of collagen could be explained by the Maillard or nonenzymatic browning reaction which occurs in stored or heated foodstuffs (Monnier, V. M. and Cerami, A., *Am. Chem. Soc.* 215, 431, 1983). In this regard, reducing sugars react nonenzymatically with the free amino groups of the proteins to form insoluble, highly crosslinked, yellow and fluorescent products. Studies on the potential occurrence of the non-enzymatic browning reaction in vivo demonstrated an age-related increase in dura and skin collagen-linked fluorescence at 440 nm (excitation at 370 nm) and chromophores absorbing above 300 nm (Monnier, V. M., Kohn, R. R., and Cerami, A., *Proc. Natl. Acad. Sci.* 81, 583, 1984) (Monnier, V. M., Vishwanath, V., Frank, K. E., Elmets, C. A., Dauchot, P., and Kohn, R. R., *New Engl. J. Med.* 314, 403, 1986). Similar spectroscopical changes could be duplicated by incubating collagen with reducing sugars such as glucose, glucose-6-phosphate or ribose (Monnier, V. M., Kohn, R. R., and Cerami, A., *Proc. Natl. Acad. Sci,* 81, 583, 1984) (Kohn, R. R., Cerami, A., Monnier, V. M., *Diabetes* 33, 57, 1984). In addition, it was demonstrated that collagen incubated with these sugars was highly crosslinked suggesting that the sugar-derived fluorophores-chromophores could act as intra- or intermolecular crosslinks (Monnier, V. M., Kohn, R. R., and Cerami, A., *Proc. Natl. Acad. Sci,* 81, 583, 1984) (Kohn, R. R., Cerami, A., Monnier, V. M., *Diabetes* 33, 57, 1984).

The potential role of the Maillard reaction in these changes was further substantiated by the observation that non-enzymatic glycosylation which initiates the Maillard reaction was increased in diabetic and aging collagen and by observations in subject with Type I (insulin-dependent) diabetes that revealed a dramatic increase in collagen-linked fluorescence (Monnier, V. M., Vishwanath, V., Frank, K. E., Elmets, C. A., Dauchot, P., and Kohn, R. R., *New Engl. J, Med.* 314, 403, 1986) (Vishwanath, V., Frank, K. E., Elmets, C. A., Dauchot, P. J., Monnier, V. M., *Diabetes* 35, 916, 1986).

Although age-related acceleration of collagen browning may be explained by the Maillard reaction, the evidence presented for support of this hypothesis has been very circumstantial. More particularly, such evidence is based on spectroscopical changes of collagen with aging and diabetes in vivo with conspicuous similarities produced by the incubation of young collagen with reducing sugars in vitro. Because of uncertainty in the exact nature of the fluorescence produced during the aging of proteins, as well as the particular nature of the protein adducts and crosslinks involved therein, the present inventors initiated a study that resulted in the present invention with the ultimate aim of elucidating the nature of the collagen-linked fluorescence which increases in aging and diabetes.

In this regard, the present inventors conducted a systematic investigation of the chemical nature of the fluorescence that accumulates in aging human collagen. Two novel fluorophores, nicknamed "P" and "M", with excitation/emission maxima at 335/385 nm and 360/460 nm, respectively, were isolated from insoluble collagen following proteolytic digestion and chromatography (Sell, D. R., and Monnier, V. M., Conn. Tiss. Res. 19, pp. 77–92, 1989). An age-related effect was noted for both types of fluorophores (i.e. the presence of the fluorophores increased with age). Although fluorophore M was borohydride reducible and unstable to acid hydrolysis, thereby suggesting that M had an iminopropene-type configuration which substantiated, but did not prove, that glucose was responsible for its origin. The fluorescence properties of the 335/385 fluorophore, i.e. fluorophore "P", were found unchanged following acid hydrolysis in 6N HCl for 24 hours at 110° C. As a result of its resistance to acid hydrolysis, a larger quantity of fluorophore P was purified from acid hydrolyzed dura mater collagen and its structure was elucidated using $^1$H-NMR, $^{13}$C-NMR and MS/MS fast atom bombardment spectroscopy. Structure elucidation of fluorophore "P" led to the discovery of a pentose-mediated protein crosslink named "pentosidine".

SUMMARY OF THE INVENTION

In one aspect, the present invention is directed to a novel imidazo [4,5b] pyridinium molecule composed of a lysine and an arginine residue crosslinked with a pentose sugar. The novel imidazo [4,5b] pyridinium compound, referred to as "pentosidine", was isolated from proteineous tissue undergoing advanced glycosylation and is believed to be one of the principal products involved in the non-enzymatic browning and/or aging of proteins. Assaying for the pentosidine molecule makes it possible to assess the degree of non-enzymatic glycosylation occurring. In addition, the pentosidine molecule may be utilized through the production of monoclonal antibodies thereto and/or the preparation of test kits, etc. for diagnostic, as well as therapeutic purposes (i.e. development of agents which inhibit the non-enzymatic browning reaction, etc.).

Structural elucidation of the pentosidine molecule indicates that its precise chemical name 3-H-imidazol [4,5b] pyridine-4-hexanoic acid, alpha amino-2 [(4-amino-4-carboxybutyl)amino), and that its structural composition is as follows:

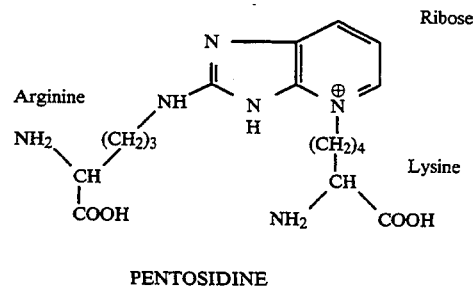

PENTOSIDINE

In a further aspect, the present invention is directed to a process for chemically synthesizing the pentosidine molecule. The structure of the isolated pentosidine molecule was confirmed by the non-enzymatic reaction of ribose with lysine and arginine residues.

Of particular interest is an improved process for synthesizing pentosidine based on the direct reaction of the Amadori product, α-t-boc-1-deoxy ribosyl-lysine (ribated lysine), with an α-amino protected L-arginine, such as α-t-boc arginine, at slightly alkaline pH's (i.e. pH about 9) with bubbling of oxygen. The α-amino protected L-arginine is a L-arginine whose α-amino group is protected by a protecting group such as Boc, Fmoc, CBZ, etc. Moreover, the ribated lysine is prepared from L-lysine whose α-amino group is also protected by a protecting group, and D-ribose. Under these conditions, the yield of pentosidine is over 12% instead of the 0.1% previously described by the inventors.

An additional aspect of the present invention is directed to a process for isolating the pentosidine molecule from insoluble collagen tissue through the acid-hydrolysis of insoluble collagen and the structural elucidation of the isolated molecule using $^1$H-NMR, $^{13}$C-NMR and various other spectroscopy techniques.

Other aspects and advantages of the present invention will become apparent to those skilled in the art upon a review of the following materials.

BRIEF DESCRIPTION OF THE DRAWINGS

The following is a brief description of the drawings which are presented for the purposes of illustrating the invention and not for the purposes of limiting same.

FIGS. 2A and 2B are graphs illustrating the absorption (FIG. 2A) and fluorescence-excitation (FIG. 2B) spectra at pH 2, 7, 9, and 12 of fluorophore P (pentosidine) isolated from native human dura mater (upper) and a synthetic incubation system of heating lysine, arginine, and ribose together at 80° C. for one hour (lower). Fluorescence-excitation spectra were monitored as follows: for the emission spectra on the right, excitation was at 335 nm, and for the excitation spectra on the left, emission was at 385 nm.

FIG. 6 is a FAB CAD MS/MS spectra of pentosidine isolated from human dura mater and a synthetic incubation system.

DETAILED DESCRIPTION OF THE INVENTION

Figures 1A, 1B, 1C:
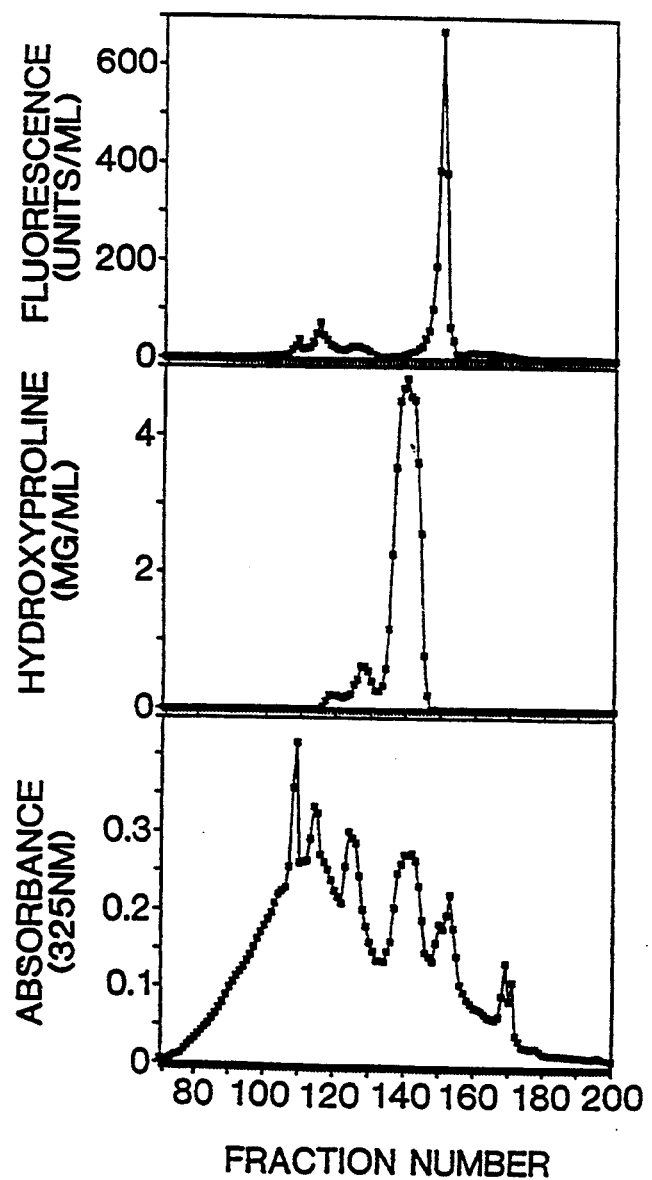
FIGS. 1A–1C are graphs illustrating the results [i.e. absorbance (FIG. 1A), hydroxyproline (FIG. 1B), and fluorescence (FIG. 1C)], produced by the fractions obtained by gel filtration on Bio-Gel P-2 of acid-hydrolyzed human dura mater. Fluorescence was monitored at excitation/emission wavelengths of 335/385 nm.

The present invention is directed to the isolation and identification of an acid resistant fluorescent molecule from the extracellular matrix of humans and other mammals. Structure elucidation of the isolated fluorescent molecule revealed the presence of an imidazo [4,5b] pyridinium molecule comprising a lysine and an arginine residue crosslinked by a pentose. Confirmation of this structural arrangement was achieved in vitro by the non-enzymatic reaction of ribose with lysine and arginine residues.

In addition, it has been determined that the newly discovered crosslink, named "pentosidine" by the inventors, can also be synthesized with isomers of ribose, arabinose, xylose, and lyxose, as well as by incubating young human collagen with these sugars at 37° C. Moreover, pentosidine was found in a variety of human tissues including plasma proteins and red blood cells. Its presence in cells grown in culture strongly suggests ribose or ribonucleotide metabolites as precursors. The unexpected discovery of pentose-mediated protein crosslinking, as well as the pentosidine crosslink, provides useful tools for the further investigation and explanation of the aging process.

More particularly, the present invention relates to the use of a novel fluorophore compound (formerly referred to as "flurophore P" and now referred to as "pentosidine") which has been isolated from human collagen undergoing advanced non-enzymatic glycosylation and identified as 3-H-imidazol [4,5b] pyridine-4-hexanoic acid, alpha amino-2[(4-amino-4-carboxybutyl-)amino]. The imidazopyridinium compound is believed to be one of the end products of the extended non-enzymatic polypeptide glycosylation reaction normally associated with the structural and functional changes in tissues that occur during the aging process, and has also been observed to occur at an accelerated rate in individuals suffering from diabetes. By identifying the occurrence of advanced glycosylation through the detection of the specified fluorophore compound of the present invention, the degree of cellular stress or injury caused by diabetes, aging, and/or uremia may be determined.

In addition, detection of the pentosidine compound may also aid in determining who among diabetic subjects is at risk of developing diabetic complications. Thus, the newly discovered fluorescent imidazopyridinium compound, or pentosidine, as well as antibodies specific to said compound, may be used in connection with various diagnostic techniques, to determine the advancement of glycosylation in protein specimens.

Furthermore, since it is generally thought that the aging effects produced by the non-enzymatic polypeptide glycosylation of the significant protein masses of the body (such as collagen, elastin, lens protein, nerve proteins, and the kidney glomerular basement membranes) is caused by the cross-linking of sugars with the amino acids of the proteins, the imidazopyridinium compound of the present invention (i.e. pentosidine) may also be utilized as an exploratory tool for the development and testing of possible agents capable of interfering with the cross-linking process, thereby inhibiting protein aging. Hence, the present invention may help reduce the incidence of pathologies involving the cross-linking of proteins such as in atherosclerosis, osteoarthritis, loss of elasticity and wrinkling of the skin, and stiffening of joints.

The present inventors have developed a process for isolating and purifying a 2-alkyl amino-4-alkyl imidazopyridinium compound (specifically, 3-H-imidizol [4,5b] pyridine-4-hexanoic acid, alpha amino-2[(4-amino-4-carboxybutyl)amino], i.e. "pentosidine"), a newly discovered imidazopyridinium compound representing a cross-link between the amino acids lysine and arginine, from a pool of insoluble human dura mater collagen following enzymatic hydrolysis and sequential purification steps utilizing Sephadex G50, paper, cation, and high performance liquid chromatography (the specific procedures and material involved in this process are more clearly set forth below in the examples). The imidazopyridinium compound was detected on the basis of its fluorescence at 385 nm upon excitation at 335 nm. Its maximum UV was at 325 nm.

Furthermore, since the compound was not destroyed by acid hydrolysis, this allowed it to be directly prepared from batch quantities of collagen. More particularly, because the pentosidine molecule was resistant to acid hydrolysis, a larger quantity of the molecule could be purified from acid hydrolyzed dura mater collagen. The compound may then be assayed by HPLC with a fluorescence detector. Structure elucidation of the fluorescent compound by $^1$H-NMR, COSY, $^{13}$C-NMR, MS/MS FAB Spectroscopy indicated the presence of an imidazopyridinium compound involving lysine and arginine and a 5-carbon moiety in the heterocyclic ring.

Moreover, in a study involving skin specimens obtained at autopsy, the imidazopyridinium compound was found to increase exponentially with age. High levels were detected in diabetic subjects with nephropathy as well as in uremic subjects without nephropathy.

In addition, the inventors have chemically synthesized their imidazopyridinium compound by the following procedure.

A mixture consisting of 0.1M D-ribose, L-lysine HCl and L-arginine at pH 7.4 was heated to 80° C. for 60 minutes and passed over Dowex 50×4 resin (H+-form). The resin was washed with one liter H₂O, 1M pyridine with 1 L of 2N NaOH. After neutralization and evaporation the concentrate was chromatographed over Bio-Gel P-2 equilibrated in 0.02M Hepes.

Fractions containing the fluorophore were further purified by HPLC using a C-18 reverse phase column and a linear gradient of acetonitrile with 0.01M of heptafluorobutyric acid (HFBA) as counterion. All fluorescence, UV, NMR, and mass spectroscopical properties of the synthetic compound were rigorously identical with those of the native compound. Yield was 0.1% under non-optimized reaction conditions.

The possibility of producing the imidazo-pyridinium compound with pentose came to the inventors as a big surprise. In this regard, the use of pentoses (i.e. ribose, arabinose, and xylose) in the total synthesis of pentosidine or any imidazopyridinium compound derived from the general reaction:

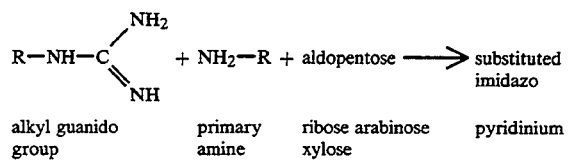

| alkyl guanido group | primary amine | ribose arabinose xylose | pyridinium | whereby R=aliphatic or aromatic rest.
is completely new. As more particularly discussed below, the in vitro synthesis of pentosidine and/or other imidazopyridine compounds is a valuable tool for researching the aging process.

In addition, the inventors have recently discovered an improved process for chemically synthesizing pentosidine based on the direct reaction of the Amadori product, α-t-boc-1-deoxy ribosyl-lysine, with α-t-boc arginine at slightly alkaline pH's (i.e. pH of about 9.0). Under these conditions, the yield of pentosidine is substantially greater (i.e. 12% versus 0.1%) than previous known processes for synthesizing pentosidine.

In the improved process discussed by the inventors, the Amadori product, Ribated-lysine (i.e. N$^\alpha$-t-Boc-N$^\alpha$-(1-deoxy-D-ribulos-1-yl)-L-lysine, was synthesized from D-ribose and α-amino protected lysine, such as Boc-lysine, using the procedure specifically set forth below in Example 2. In essence, a suspension of about 0.005 mol of Boc-lysine (N$^\alpha$-t-Boc-L-lysine) and about 0.04 mol of D-ribose in 100 ml of methanol was refluxed for approximately 45 minutes. The methanol was removed to yield a dark gum. The residue was subsequently dissolved in about 10 ml of water and loaded onto a Dowex 50w×4 column (H+-form). The column was eluted with 0.2M pyridine formate (pH 3.25) and the effuent was tested for the present of Ribated-lysine by thin layer chromatography. Fractions corresponding to the ribated-lysine were combined and concentrated.

The Amadori product, i.e. about 0.1M solution of the Ribated-lysine, was then incubated with about 0.1M of an α-amino protected arginine, such as Boc-arginine (N$^\alpha$-t-Boc-L-arginine), at a slightly alkaline pH for 48 hours at 65° C. according to the following reaction:

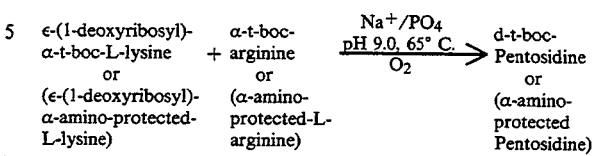

Pentosidine was then subsequently purified by HPLC using a C-18 reverse phase column and a linear gradient of acetonitrile with heptafluorobutyric (HFBA) as a counterion. The pentosidine produced by such a process was identified with the original pentosidine in terms of U.V., fluorescence, NMR and MS/MS spectrum analysis. See Example 2 below.

The formation of pentosidine from Ribated-Lysine and Boc-arginine at different pH levels was compared (see Graph 2) with the formation of pentosidine from D-glucose, D-ribose and glucated-lysine when incubated with Boc-lysine and/or Boc-arginine at different pH's. The results clearly indicated that the production of pentosidine from Ribated-lysine and arginine produced by far the greatest yield (over 12% yield) and that an increase in pH and bubbling of oxygen gas also enhanced the production yield.

The specific procedures and materials used in the isolation, characterization, and chemical synthesis of the pentosidine compound of the present invention are set forth below in the following illustration examples.

EXAMPLE 1

Methods and Procedures

Preparation of Pentosidine from Dura Mater

The starting material consisted of insoluble human dura mater (60 g wet weight) determined to contain greater than 95% collagen on the basis of hydroxyproline content. Hydroxyproline was quantitated as described in Hamlin, et al. (i.e. Hamlin, C. R., Luschin, J. H., and Kohn, R. R., *Exp. Gerontol.* 13, pp. 415–523, 1978) and assumed to make up 14% of the collagen by weight (Hamlin, C. R., and Kohn, R. R., *Biochem. Biophys, Acta*, 236, pp. 458–467, 1971). The dura mater was homogenized twice in phosphate-buffered saline (PBS, pH 7.4), extracted for 24 hours in 2:1 chloroform/methanol, and acid-hydrolyzed under reflux and nitrogen for 36 hours in 6 liters of 6N HCl. The acid was evaporated at 40° C. The residue was dissolved in water and pH adjusted to 7.4 (NaOH). The material was applied to a 5×150 cm column of Bio-Gel P-2 fine (Bio-Rad Laboratories, Rockville Centre, N.Y.) equilibrated with 0.02M Hepes (pH 7.4) containing 0.15M NaCl. Fifteen milliliter fractions were collected at a flow rate of 1 ml/min. Fractions containing the 335/385 fluorophore were pooled, adjusted to pH 8.5 with NaOH and rotary evaporated. The fluorophore was extracted with methanol to remove some of the salts. The methanol, in turn, was evaporated and the residue dissolved in 10 ml of water and acidified with concentrated HCl. Purification was achieved by multiple injections/peak collections using reverse-phase C-18 HPLC and a water/acetonitrile solvent containing consecutively trifluoroacetic acid (TFA), n-heptafluorobutyric acid (HFBA), and again TFA as counterions. The final product was judged pure by virtue of a single ninhydrin positive spot on paper chromatography and a single UV and fluorescent HPLC peak under various chromatographic conditions using a reverse-phase column.

Synthesis and Purification of Pentosidine from a Synthetic System

Three liters containing 100 mM each of L-arginine, L-lysine and D-ribose, at pH 7.3, were heated for 1 hr at 80° C. The cooled mixture was poured onto a Buchner funnel filled with Dowex 50×4-400 ion-exchange resin (Aldrich Chem. Co., Inc., Milwaukee, Wis.) equilibrated according to conditions of Boas (Boas, N. F., *J. Biol. Chem.*, 204, pp. 553-563, 1953). The resin was washed with 2 liters each of water and 1M pyridine, followed by elution of pentosidine-containing material with 1 liter of 2N NaOH. The material was then adjusted to pH 7.4 with HCl, concentrated by rotary evaporation, passed through a Bio-Gel P-2 column and purified by HPLC as described above. The material was also chromatographed on Whatman 17 Chr paper (Whatman Inc., Clifton, N.J.) using 1:1 water/pyridine. Upon elution from the paper, the material was reinjected and collected by reversed-phase HPLC using TFA as the counterion.

High Performance Liquid Chromatography (HPLC)

A Waters HPLC (Waters Chrom. Div., Milford, Mass.) with Model 510 pumps, U6K injector, and a 680 controller was used. The effluent was monitored at 385 nm (excitation at 335 nm) with a J4-8202 Aminco-Bowman spectrophotofluorometer (SLM Instru., Inc., Urbana, Ill.) equipped with a 9 μl continuous flow cell. Separations were made on either a 4.6 mm (analytical) or 1.0 cm (semi-preparative) ×25 cm Vydac 218TP (10 micron) C-18 column (The Separations Group, Hesperica, Calif.) by application of a linear gradient system of 0-17% acetonitrile from 10 to 97 min,. with either TFA or HFBA as counterion at a flow rate of 1 (analytical) or 2 ml/min (semi-preparative). Pyridoxamine (Sigma Chem. Co., St. Louis, Mo.) which autofluoresces was used as an internal standard.

Figure 5:
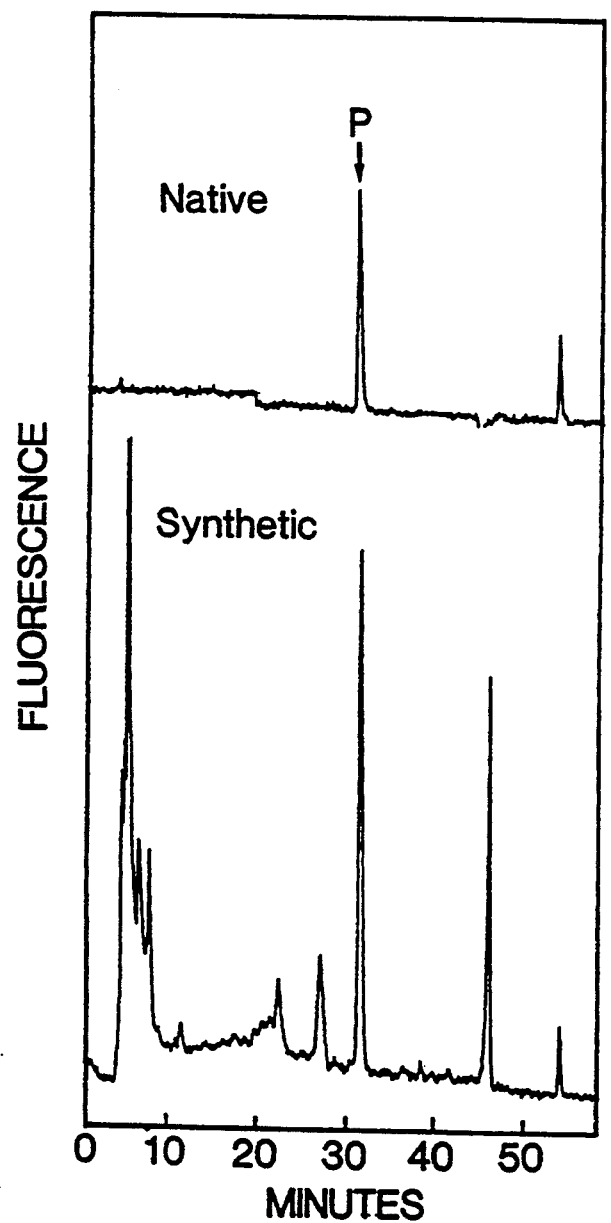
FIG. 5 is a graph showing a comparison of a HPLC chromatogram of purified pentosidine (P) from native dura mater to that of unpurified synthetic material. Separations were made on a 0.46×25 cm Vydac 218 TP C-18 column by application of a linear gradient of 10-17% acetonitrile in water applied from 0-35 minutes at a flow rate of 1 ml/min. with 0.01M HFBA as the counterion. Fluorescence was monitored as of FIG. 1.

For analytical purpose, the HPLC program was shortened such that a linear gradient of 10-17% acetonitrile was applied from 0-35 min. with HFBA as the counterion (see FIG. 5).

Incubation of Sugars with L-lysine and L-arginine In Vitro

Sugars were incubated with L-lysine and L-arginine at 80° C. for 1 hour in PBS. Each sugar and amino acid were present at concentrations of 100 mM in a total volume of 2 ml in 13×100 mm test tubes placed in a Reacti-Therm heating block (Pierce Chem. Co., Rockford, Ill.).

In Vitro Incubation of Young Collagen with Pentoses

A pool of young dura mater (average age 15 years) obtained at autopsy was homogenized in PBS and extracted for 24 hours in 2:1 chloroform/methanol. Dry blotted tissue (0.5 g wet weight) was incubated with 100 mM each of the pentose sugars, L-arginine and L-lysine in 12 ml of PBS containing 10 μl each of toluene and chloroform. After incubation at 37° C. for 6 days, 0.3 g wet tissue weight was withdrawn from each tube and washed three times with 5 ml portions of PBS and water, respectively. Samples were acid-hydrolyzed in 2 ml of 6N HCl for 24 hours. Following evaporation of the acid, the material was reconstituted in 1 ml of water. Hydroxyproline content was determined as described (Hamlin, C. R., Luschin, J. H., and Kohn, R. R., *Exp. Gerontol.* 13, pp. 415-523, 1978) and equalized among samples.

Determination of Pentosidine in Tissues

Tracheal cartilage, cortical bone (iliac crest), aorta, kidney, cardiac muscle, lung, liver, skin, dura mater and lens were obtained at autopsy from elderly subjects. Cartilage, bone and aorta were decalcified. All tissues were minced and extracted with 4-5 changes of PBS before lyophilization. Red blood cells, obtained by centrifugation of human blood, were washed three times in PBS and lyophilized. The following were gifts: purified isolated human renal glomerular basement membrane from Dr. Edward C. Carlson (University of North Dakota); human and rat-cultured glomerular mesangial cells from Dr. John R. Sedor (Case Western Reserve University, School of Medicine); and mixed human fibroblasts cultured for 14 days on rat tail tendon collagen-coated petri dishes from Dr. Irwin A. Schafer (Case Western Reserve University, Cleveland Metropolitan General Hospital). Human placental, bovine Achilles tendon and calf skin collagens were purchased from Sigma Chem. Co. (St. Louis, Mo.).

Approximately 15 mg of each sample were acid-hydrolyzed in 2 ml of 6N HCl for 24 hours. The acid was evaporated and pentosidine was quantitated by HPLC after reconstituting samples with water.

Spectroscopy

Absorption spectra were recorded with a Hewlett-Packard (HP) 8452A diode array spectrophotometer connected to an IBM PC/AT computer (Hewlett-Packard, Inc., Avondale, Pa.; IBM Corp., Boca Raton, Fla.). Fluorescence spectra were recorded with a J4-8202 Aminco-Bowman spectrophotofluorometer (SLM. Instru., Inc., Urbana, Ill.).

Samples for proton NMR spectroscopy were exchanged three times with deuterium oxide ($D_2O$) under a nitrogen atmosphere. The sample contained in 400 μl of 100% $D_2O$ was transferred to a 5 mm NMR tube and scanned for 10 min. in a 400 MHz spectrometer (MSL 400, Bruker Instru., Inc., Billerica, Mass.). The following conditions were used (FIG. 3): spectrometer frequency, 400.13 MHz; spectral width, 1 ppm=400.13 Hz; Hz/point=0.244; acquisition time, 2.048 s (native), 1.024. s (synthetic); number of scans, 944 (native), 400 (synthetic); temperature, 297° K.; recycle delay, 5 s; pulse width, 6.65 μs corresponding to 90° TPS(3-(trimethylsilyl)-1-propane-sulfonic acid) was used as an internal standard. For two-dimensional H,H-correlated (COSY) spectroscopy, the sample was scanned overnight.

Mass-spectrometry analyses were performed by Dr. Douglas Gage at the NIH mass-spectrometry facility in the Department of Biochemistry, Michigan State University, East Lansing, Mich. Molecular weights were determined by fast atom bombardment (FAB) spectroscopy with a JEOL HX 110HF double focusing mass spectrometer. Analysis was initially conducted at low resolution (1000) at accelerating voltage of 10 KV. Samples were dissolved in 0.1% TFA and mixed with an equal volume of glycerol. Ions were formed by FAB with a 6 KeV beam of Xe atoms. Spectra which were generated by FAB CAD MS/MS analysis (collisionally activated dissociation tandem mass spectrometry) made use of a JEOL DA-5000 data-system-generated linked scans at constant B/E. Helium was used as the collision gas in a cell located in the first field-free region and the pressure was adjusted to reduce the abundance of the parent ion by 75%. FAB high resolution mass analysis was performed at resolution 20,000 by peaking matching on the glycerol matrix ion at M/Z 369.

Results

Isolation and Purification of Pentosidine from Tissue.

A pool of dura mater (600 g wet weight) obtained at autopsy from elderly donors (average age 77 years) was acid-hydrolyzed and fractionated by Bio-Gel P-2 gel filtration chromatography (see FIG. 1). The bulk of the fluorescence material eluting together with salt was pooled, dried by evaporation and extracted into methanol. After evaporation and reconstituting in water, the fluorescent material was purified to homogeneity by repeated injections on reverse phase HPLC. Total fluorophore recovered was 1 mg.

Structure Elucidation of Pentosidine.

The fluorophore was characterized by absorption, fluorescence, $^1$H-NMR, and mass spectroscopical properties. Its UV and fluorescence maxima (FIG. 2, top) were identical with those of the previously described unhydrolyzed fluorophore (Sell, D. R., and Monnier, V. M., Conn. Tiss. Res. 19, pp. 77–92, 1989) suggesting that no damage occurred as a consequence of hydrolysis. A peculiarity was noted in fluorescence-excitation intensities which varied with pH, being highest at pH 2 and 12, and completely quenched at pH 9 (see FIG. 2).

Crucial structural information was obtained from the $^1$H-NMR spectrum (see FIG. 3, top; also FIG. 4) which showed two doublets, a and b at 7.78 and 7.94 ppm, respectively, that were coupled with the triplet c at 7.22 ppm (FIG. 4) as revealed by a COSY experiment (not shown). This configuration suggested the presence of three aromatic protons in a pyridinium molecule with substitutions in positions 5 and 6. The two uncoupled triplets at 3.9 and 3.95 ppm suggested the presence of two α-protons compatible with the presence of two amino acids. Two other triplets (d and e in FIG. 3) were observed at 3.6 and 4.6, both coupled with aliphatic protons at 2.0 ppm. By comparison with published spectra of pyridinoline (Fujimoto, D., Moriguchi, T., Ishida, T., and Hayashi, H., Biochem. Biophys. Res. Commun. 84, pp. 52–57, 1978) (Deyl, Z., Macek, K., Adam, M., and Vancikova, Biochem. Biophys. Acta, 625, pp. 248–254, 1980) (Ogawa, T., Tsuda, T.O.M., and Kawonishi, Y., Biochem. Biophys. Res. Commun., 107, pp. 1252–1257, 1982), lysine emerged as a likely component of the fluorescent molecule.

FAB high resolution mass spectrometry showed a M/Z of 379.2069 compatible with the empirical formula $C_{17}H_{27}N_6O_4$. Taken together, the data suggested the possible presence of an imidazo [4,5b] pyridinium ring comprising a five-carbon moiety (highlighted as bold lines in the structure below) with a lysine and arginine side chain. This configuration suggested that crosslinking of the two amino acids might have occurred as a consequence of Maillard reaction with a pentose.

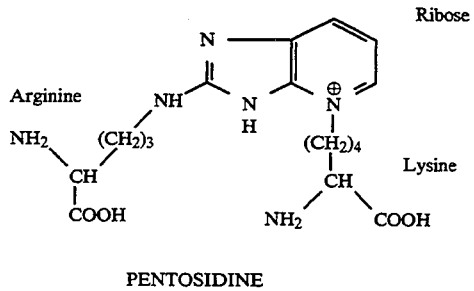

PENTOSIDINE

In Vitro Synthesis of Pentosidine

In order to confirm the pentose-derived nature of the native fluorophore 100 mM each of L-lysine, L-arginine and D-ribose were heated for 1 hour at 80° C. Injection of a small amount of this synthetic material on HPLC revealed a major fluorescent peak co-eluting with the native fluorophore. (see FIG. 5) In order to substantiate the proposed structure, the synthetic fluorophore was prepared preparatively and purified. Total yield was 21 mg; i.e., 0.02% of the reactants.

Spectroscopical Comparison of Native and Synthetic Pentosidine

The synthetic fluorophore showed the same UV and fluorescence spectra, including pH effects, as those of the native fluorophore (FIG. 2, bottom). The molar absorption coefficients of the native and synthetic compounds were determined to be 4522 and 4195 in 0.1N. HCl, respectively.

Figure 3:
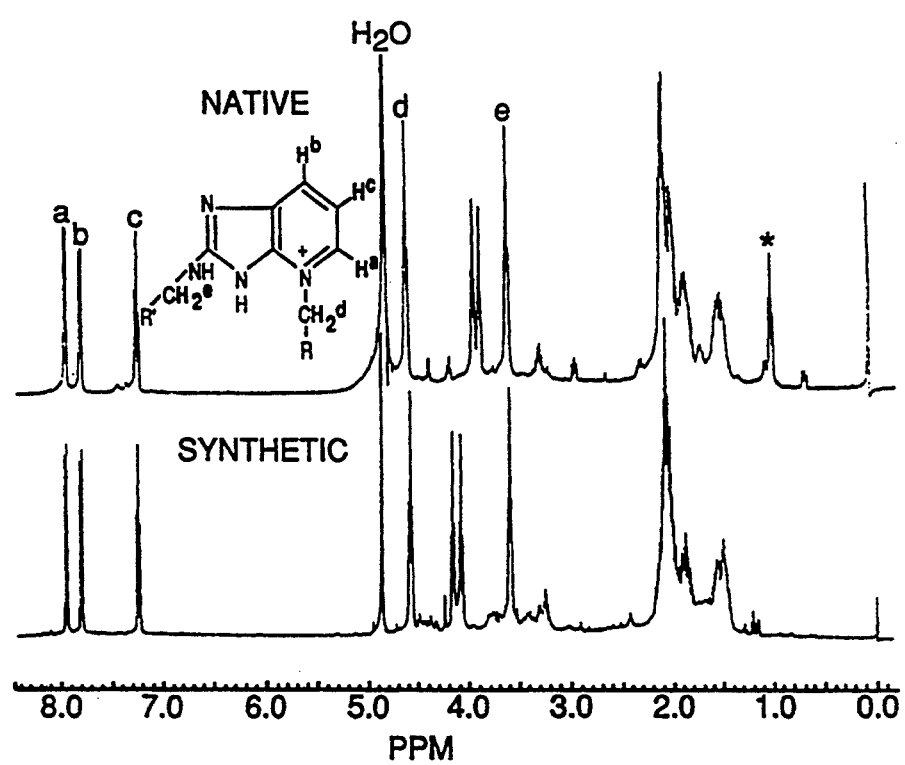
FIG. 3 is a $^1$H-NMR spectra of pentosidine isolated from human dura mater and a synthetic incubation system.
Figure 4:
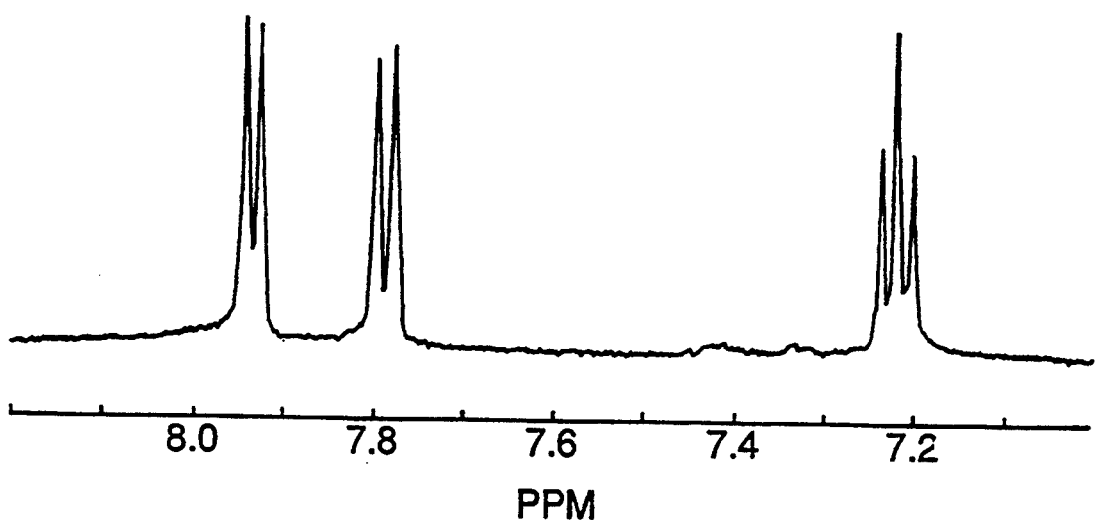
FIG. 4 is a expanded 7.1–8.2 portion of the $^1$H-NMR spectrum from FIG. 3 (native).

$^1$H-NMR spectra of the synthetic and native fluorophores were similar except for a small shift of the α-proton triplets at 4.08 and 4.16 ppm attributable to a pH or concentration effect (FIG. 3). Other structural assignments are shown in FIG. 3.

Fragmentation patterns (FIG. 6) of synthetic and native compounds obtained by FAB CAD MS/MS analysis were also identical except for minor differences in peak intensities attributed to differences in operating conditions of the instrument since analyses were made 6 months apart. FAB high resolution analyses showed measured M/Z of 379.2069 and 379.2091 for the native and synthesized fluorophores, respectively (±0.4 ppm instrument error). The calculated mass of the proposed compound is 379.4392.

Origin of the Imidazo [4,5b] Pyridinium Ring

The spectroscopical data from the native and synthetic fluorescent molecules leaves little doubt as to the nature and structure of the newly discovered crosslink. The complete aromatization of ribose in the formation of the pyridinium ring, however, suggests that the isomers of ribose; i.e., arabinose, xylose and lyxose, can also mediate the same reaction. To test for this possibility, and to investigate the structure requirements of reducing sugars for the formation of the fluorescent molecule, hexoses and pentoses were reacted with equimolar amounts of Llysine and L-arginine at 80° C. for 1 hour. The results are set forth below in Table I.

TABLE I

The Effects of Incubation of Various Sugars with Lysine and/or Arginine for 1 Hour at 80° C. on the Formation of Pentosidine
(Quantitated according to the conditions of FIG. 5)

| Sugar (100 mM) | L-Lysine (100 mM) | L-arginine (100 mM) | Pentosidine (nmole/ml) |
|---|---|---|---|
| D-Galactose | + | + | ND |
| D-Glucosamine | + | + | ND |
| D-Glucose | + | + | ND |
| D-Fructose | + | + | ND |
| D-Fucose | + | + | ND |
| 2-Deoxy-D-Ribose | + | + | <0.1 |
| D-Ribose-5-Phosphate | + | + | <0.1 |
| D-Ribulose | + | + | <0.1 |
| D-Xylulose | + | + | <0.1 |
| D-Xylose | + | + | 2.9 |
| D-Arabinose | + | + | 4.4 |
| D-Lyxose | + | + | 3.0 |
| D-Ribose | + | + | 5.2 |
| D-Ribose | + | − | ND |
| D-Ribose | − | + | ND |

(+) added, (−) not added, (ND) not detected.

Figure 7:
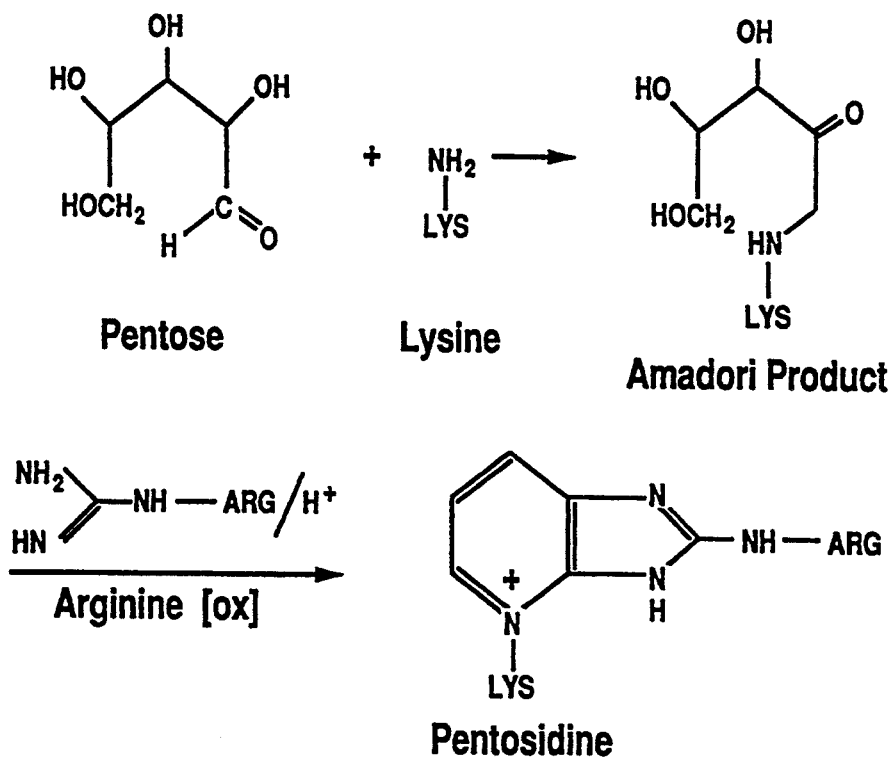
FIG. 7 is a chart indicating the proposed mechanism for the formation of pentosidine.

The results in Table 1 indicate that all three aldopentoses (xylose, arabinose and lyxose) could serve as precursors of the imidazo [4,5b] pyridinium ring. This observation led the present inventors to name the fluorophore "pentosidine". None of the hexoses tested, however, were able to generate this compound. Extremely low levels were detected with 2-deoxy-Dribose, ribose-5-phosphate and pentuloses suggesting that commercial preparations of these sugars contain small amounts of pentosidine precursors. Pentosidine could also be synthesized by direct incubation at physiological pH and temperature of young collagen with pentoses (Table II). The highest yield was obtained with D-ribose. The addition of free lysine or arginine blocked impart the synthesis of pentosidine presumably by trapping of free ribose or intermediates of the Maillard reaction that might be involved in pentosidine synthesis (Table II, Experiment 1). A possible biosynthetic mechanism for pentosidine formation is depicted in FIG. 7.

TABLE II

The Effects of Incubation of Young Collagen With
Pentose Sugars, Lysine, and/or Arginine
for 6 Days at 37° C. on the
Formation of Pentosidine[a]
(Quantitated according to the conditions of FIG. 5)

| Pentose (100 mM) | L-Lysine (100 mM) | L-Arginine (100 mM) | Pentosidine (pmole/mg Collagen) |
|---|---|---|---|
| Experiment 1 | | | |
| None | − | − | 57 |
| D-Ribose | − | − | 326 |
| D-Ribose | + | − | 131 |
| D-Ribose | − | + | 118 |
| D-Ribose | + | + | 107 |
| None | + | + | 69 |
| Experiment 2 | | | |
| None | − | − | 46 |
| D-Xylose | − | − | 125 |
| D-Arabinose | − | − | 109 |
| D-Ribose | − | − | 288 |
| D-Lyxose | − | − | 168 |

(−) no added, (+) added

Pentosidine in Various Biochemical Specimens

Figure 8:
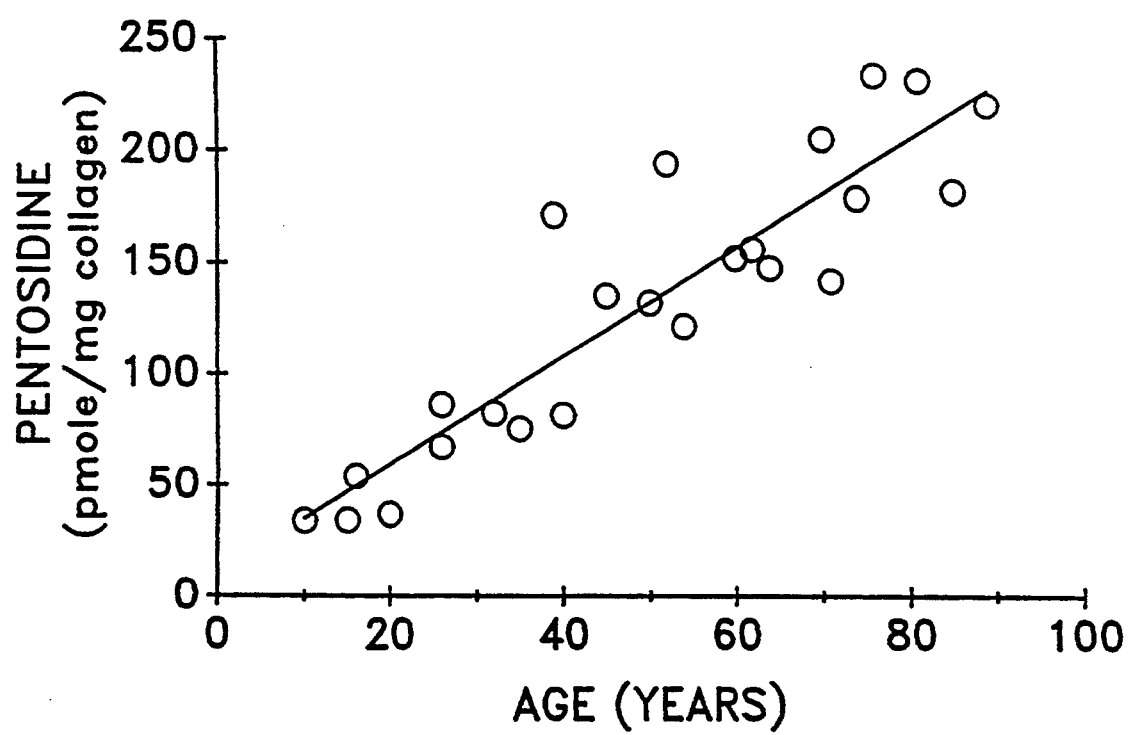
FIG. 8 is a graph showing the relationship of the pentosidine level as a function of age in human dura mater. The assay was conducted according to conditions of FIG. 5. Line equation: pentosidine (pmol/mg collagen)=10.8+2.43 (age). N=24, $p<0.001$, r=91.

The presence of pentosidine was studied in a variety of tissues by HPLC. Quantitation in aging human dura mater revealed a linear 10-fold increase throughout life which reached approximately 250 pmol/mg collagen in late life (see FIG. 8). In a separate study on pentosidine level in human skin, the progression was exponential in late life but reached only 75 pmol/mg collagen suggesting a higher turnover of skin than dura mater. Pentosidine was also detected in crude preparations of human heart, aorta, lungs, cartilage, bone, tendon, liver, renal cortex and medulla, and a pure preparation of glomerular basement membrane obtained after proteolytic digestion (see Table III below). The question of whether pentosidine in these tissues originated primarily from cellular or extracellular matrix was not investigated at this point. However, pentosidine was also detected in red blood cell and plasma proteins (Table III) suggesting that the ability of pentoses to crosslink proteins is not limited to the extracellular matrix. No pentosidine was detected in commercial preparations of Type I, III, IV and V soluble collagens, but a small level was detected in a commercial preparation of insoluble Type I collagen obtained from bovine tendon (Table III).

TABLE III

Summary of Pentosidine Levels in Different Tissues
(Quantitated according to the conditions of FIG. 5)

| Tissue | pmole Collagen (mg) | pmole Tissue (mg) |
|---|---|---|
| HUMAN: | | |
| Dura Mater | 151 | 117 |
| Skin | 29 | 27 |
| Tracheal Cartilage | 182 | 142 |
| Cortical Bone | 49 | 9 |
| Aorta | 72 | 33 |
| Cardiac Muscle | 139 | 29 |
| Lung | 116 | 29 |
| Liver | 330 | 12 |
| Kidney Cortex | 42 | 17 |
| Kidney Medulla | 63 | 25 |
| Purified Isolated Glomerular Basement Membrane | 35 | 21 |
| Red Blood Cells | — | 10 |
| Blood Proteins | — | 8 |
| Lens | — | 0.7 |
| Placenta (Commercial Types III, IV, V Soluble Collagens) | ND[a] | ND |
| OTHER: | | |
| Calf Skin (Commercial Type I Soluble Collagen) | ND | ND |
| Bovine Tendon (Commercial Type I Insoluble Collagen) | 10 | 7 |
| CELL CULTURE: | | |
| Human Fibroblasts[b] | 345 | — |
| Collagen Matrix (Blank)[c] | 25 | — |

[a]ND, not detected
[b]Mixed fibroblasts cultured for 14 days on rat tail tendon collagen-coated petri dishes
[c]Represents a control consisting of collagen-coated petri dishes containing medium incubated for 14 days without cells.

A very low level was detected in the human ocular lens, a tissue with a metabolism significantly different from that of tissues rich in nucleated cells. Finally, and unexpectedly, pentosidine was detected in human fibroblasts grown in culture (Table III). A high quantity was also detected in cultures of human glomerular mesangial cells grown in a pentose-free medium. However, additional studies will be needed to determine its origin.

Discussion

The discovery of an age-related accumulation of pentosidine in human extracellular matrix is the first molecular evidence for the involvement of reducing sugars in protein crosslinking. In preliminary studies, Kohn, et al. (Kohn, R. R., Cerami, A., and Monnier, V. M., *Diabetes* 33, pp. 57-59, 1984) demonstrated that rat tail tendons incubated with reducing sugars became rapidly crosslinked. The crosslinking rate as measured by tail tendon breaking time in urea was much greater for ribose than glucose and was accompanied by formation of collagen-linked fluorescence. While the study which resulted in the present invention was in progress, Tanaka, et al. (Tanaka, S., Avigad, G., Eikenberry, E. F., and Brodsky, B., *J. Biol. Chem.*, 263 pp. 17650-17657, 1988) reported the isolation of highly fluorescent dimers of α chains crosslinked in triple-helical regions of ribose-incubated rat tail tendon collagen.

Although these studies suggested that the pentose could mediate crosslinking in vitro, the discovery of pentose-mediated crosslinking in vivo is quite unexpected and raises a number of biochemical and biological questions concerning the origin and role of pentosidine. The absence of detectable pentosidine in solutions of glucose incubated for 1 hour at 80° C. with equimolar lysine and arginine suggests that glucose and its Amadori product are unlikely precursors of pentosidine. However, little browning was yet detectable after 60 min. and a fragmentation of glucose or its Amadori product into a pentose upon prolonged reaction is not excluded. Similarly, studies will be needed to evaluate the possible contribution of glyco-conjugates to pentosidine recovered from acid-hydrolyzed biological specimens. In this sense, the data presented in Table III should be considered as preliminary. Albeit this word of caution, there is little doubt that pentosidine forms spontaneously in aging since it increased in an enzymatic hydrolysate of human dura mater with age (Sell, D. R., and Monnier, V. M., Conn. Tiss. Res. 19, pp. 77–92, 1989).

In contrast to the extensive literature on blood and tissue levels of glucose, however, only a scant amount of information is available on the source and the level of free pentoses in tissue and body fluids. All three sugars, ribose, xylose and arabinose, have been detected in the urine with excretion rates of 5, 8.5 and 14 $\mu$g/min, respectively (Bell, D. J., and Talukder, M., Q-K, Clin. Chim. Acta, 40, pp. 13–20, 1972). Total pentose level in human plasma has been estimated at 44 $\mu$M (McKay, E., Clin. Chim. Acta, 10, pp. 320–329, 1964), but no information is available on the concentration of particular pentoses.

A number of observations suggest that ribose or one of its metabolites is a likely precursor of pentosidine in vivo. First, of all tested pentoses, ribose was the most reactive sugar in the synthesis of pentosidine (Table II). This observation is in agreement with previous determinations of the chemical reactivity of ribose (Overend, W. G., Peacoke, A. R., and Smith, J. B., J. Chem. Soc., pp. 3487–3492, 1961). Second, free arabinose and xylose are thought to arise primarily from alimentary sources, mainly through the ingestion of fruits and the bacterial degradation of xylans in the intestine (McKay, E., Clin. Chim. Acta, 10, pp. 320–329, 1964) (Date, J. W., Scand. J. Clin. Lab Invest., 10, pp. 155–162, 1958). Thus, it is unlikely that these sugars would explain pentosidine formation in cell culture. Third, lyxose has been only associated with heart muscle (Pailares, E. S., and Garza, H. M., Arch. Biochem., 22, pp. 63–65, 1949). Finally, the detection of high pentosidine levels in cell culture (Table III) is strongly suggestive for leakage or release of significant amounts of free ribose or its metabolites as a consequence of accelerated ribonucleotide turnover, cellular turnover or cell death. In this regard, a possible source for a precursor of pentosidine could come from ADP-ribosylation reactions which play a crucial role in many cellular functions, including DNA repair mechanisms which are thought to play a role in cellular aging (Ueda, K., and Hayaisha, O., Ann. Rev. Biochem. 54, pp. 73–100, 1985). Yet, these propositions are speculations that will need to be addressed experimentally.

Pentosidine is of significance for gerontological research for two reasons. First, pentosidine may contribute to the age-related stiffening of tissues by crosslinking of the extracellular matrix. The extent of crosslinking can be estimated by the relative amount of crosslinks found in old human dura mater collagen assuming a molecular weight of 300,000 for the triple-helical region. The presence of 250 pmol/mg collagen translates into 7.5% modification (0.075 mol/mol of collagen). This would be compatible with a 2 to 3-fold decrease in collagen digestibility according to the estimate by Vater, et al. (Vater, C. A., Harris, E. D., and Siegel, R. C., Biochem. J., 1881, pp. 639–645, 1979). It is also possible that additional pentose derived crosslinks would form during aging because pentosidine was only one of many compounds present in the reaction mixture of arginine, lysine and ribose. Second, pentosidine may serve as a molecular marker of the aging process and its availability should greatly facilitate studies on longevity and the potential role of Maillard-mediated damage by pentoses in the life-span limiting process.

EXAMPLE 2

Improved Synthesis of Pentosidine Based On the Direct Reaction of Ribated Lysine and $\alpha$-t-Boc-Arginine Methods and Procedure Chemicals D-glucose, D-ribose, furfural, aminoguandine and trifluoroacetic acid were purchased from Aldrich (Milwaukee, Wis.). Bovine serum albumin (fatty acid and globulin free, Sigma Cat No. 0281) and heptafluorobutyric acid were purchased from Sigma (St. Louis, Mo.). Boc-lysine and Boc-arginine were purchased from Bachem (Torrance, Calif.). HPLC grade water, methanol and acetonitrile from Fisher Scientific Co., (Pittsburgh, Pa.).

General Methods $^1$H-NMR spectra were recorded with a 400 MHz spectrometer (MSL 400, Bruker instruments Inc., Billerica, Mass.). Samples for proton NMR were carried out either in deuterated chloroform or water. Tetramethylsilane (TMS) or 3-(trimethylsilyl) propionic acid (DSS) were used as internal standards.

Absorption spectra were recorded with a Hewlett-Packard 8452A diode array spectrophotometer connected to an IBM PC/AT computer (Hewlett-Packard, Inc., Avondale, Pa., IBM corp. Boca Raton, Fla.). Fluorescence spectra were recorded with a J4-8202 Aminco-Bowman spectrophotofluorometer (SLM Instruments Inc., Urbana, Ill.).

Mass spectrometry analyses were performed by Dr. Douglas Gage at the National Institute of Heal Mass Spectrometry Facility (Department of Biochemistry, Michigan State University, East Lansing, Mich.). Molecular weights were determine by fast atom bombardment (FAB) spectroscopy with a JEOL HX 1100HF double focusing mass spectrometer. Analysis was initially conducted at low resolution (1000) at accelerating voltage of 10 kV. Samples were dissolved in 0.1% trifluoroacetic acid and mixed with an equal volume of glycerol. Ions were formed by FAB with a 6 keV beam of Xe atoms. FAB-high resolution mass analysis was performed at resolution 20,000 by peak matching on the glycerol matrix ion at m/z 369.

Thin layer chromatography (TLC) was performed on aluminum sheets precoated with silica gel 60 $F_{254}$ (0.2 mm Merck). Flash chromatography was performed using 40–65$\mu$ (400–230 mesh) silica gel 60 (E. Merck, No 9385).

High Performance Liquid Chromatography (HPLC)

HPLC was performed with a Waters HPLC system (Waters Chromatography Div., Milford, Mass.) equipped with a model 510 dual pump system, U6K manual injector, model 712 WISP automatic injector, and an automated gradient controller. The effluent was monitored with a J4-8202 Aminco-Bowman spectrofluorophotometer (SLM Instruments Inc., Urbana, Ill.) or with a Waters 470 fluorescence detector. Chromatograms were recorded on a Waters 740 data module.

Analytical separations were carried out using 4.6 mm (analytical) Vydac (218TP104) $C_{18}$ column by application of a linear gradient of 10–17% of acetonitrile from 0–35 min with 0.01% heptafluorobutyric acid (HFBA) as a counterion at a flow rate of 1 ml/min. Preparative HPLC was achieved with a 2.2×25 cm (semi-preparative) Vydac (218TP1022) $C_{18}$ column by application and a linear gradient of 0–30% acetonitrile from 0–65 min with trifluoroacetic acid (0.01%) as counterion and a flow rate of 2 ml/min or with a preparative 2.2×2.5 cm Vydac (218TP1022) $C_{18}$ column by application and a linear gradient of 0–30% acetonitrile from 0–50 min with trifluoroacetic acid as counterion and a flow rate of 5 ml/min.

Preparation of $N^\alpha$-t-Boc-$N^\alpha$-(1-deoxy-D-ribulos-1-yl)-L-lysine (Ribated lysine):

Ribatedlysine ($N^\alpha$-t-Boc-$N^\alpha$-(1-deoxy-D-ribulos-1-yl)-L-lysine) was synthesized from D-ribose and Boc-lysine using the following procedure. A suspension of 1.32 g (0.005 mol) of Boc-lysine and 6.1 g (0.04 mol) of D-ribose in 100 ml of methanol was refluxed for 45 min. Methanol was removed using rotary evaporator to yield a dark gum. The residue was dissolved in 10 ml of water and loaded onto a Dowex 50W×4 column (75×2.5 cm). The column was eluted with 0.2M pyridine formate (pH 3.25) and the effluent was tested for the present of Ribated-lysine by thin layer chromatography using solvent system containing 50:6:10 butanol:acetic acid:water and ninhydrin spray. Fractions corresponding to ribated lysine were combined, concentrated and chromatographed using flash column chromatography (20 cm×5 cm) with silica gel. Elution with 3:1 methanol: Ethyl acetate afforded the Amadori product in 45% yield as a white sticky sol id. TLC Rf in butanol: acetic acid: water 50:6:10 was 0.33. $^1$NMR absorbances $^1$H-NMR($D_2O$) $\delta 1.29$(s, 9H—$CH_3$), $\delta 1.61$(m,4H,m—$CH_2$—$CH_2$), $\delta 3.1$ (t,J 10,2H,—$CH_2N$), $\delta 3.21$ (s,2H, —$COCH_3$), $\delta 3.7$–4.5(m, 7H,CHOD & CHOOD). MS m/z (relative intensity) 379(100%)M+H, other peaks at 361.1(16%), 323 (89.28%) 305(12.5%) 298 (5%) 287.1(40%) 247.2(30%).

Comparative study of formation of pentosidine from D-glucose, D-ribose, Glucated-lysine and Ribated-lysine.

Well oxygenated 0.1M solutions of D-ribose, D-glucose, Glucated-lysine and Ribated-lysine were incubated with 0.1M of Boc-lysine ($N^\alpha$-t-Boc-L-lysine) and Boc-arginine ($N^\alpha$-t-Boc-L-arginine) in phosphate buffer (0.5M in sodium) at pH's of 4, 7.4 and 9 and 65° C. for 48h. Aliquots were removed at regular intervals and refrigerated (−4° C.). After 48 hours, the samples were analyzed for pentosidine by HPLC according to the process set forth below.

Role of acid hydrolysis in Pentosidine formation 0.1M solution of Ribated-lysine was deblocked with trifluoroacetic acid (3ml) overnight at room temperature. The trifluoroacetic acid was removed under vacuo and the free Amadori product was incubated with unprotected L-arginine (0.1M) in phosphate buffer (0.5M) at pH 7.4 and 65° C. for 48 h. After incubation, the reaction mixture was divided into two portions. Once portion was left untouched while the other was hydrolyzed with 6N HCl at 110° C. for 10 min. Both portions were dried down and reconstituted in equal volume of solvent and HPLC analysis was carried out under identical analytical conditions.

Pentosidine Purification and/HPLC Analysis

The aliquots produced by the comparative study defined above were loaded onto a 60×5 cm ion exchange column filled with equilibrated Dowex 50×8-400 ion exchange resin (Aldrich Chemical Co., Milwaukee, Wis.). The column was sequentially eluted with distilled water (1000 ml), 1M pyridine (2000 ml) and 1M pyridine acetate (2000 ml) pH 6. Fractions of 10 ml were collected and spotted on filter paper to check for ninhydrin positive material and analyzed for fluorescence (335/385 nm). Pentosidine eluted with the pyridine acetate buffer in fractions 26–50. These were pooled and concentrate do to dryness. The residue was treated with 50 ml of trifluoroacetic acid and left to stand overnight, dried and loaded onto a column of neutral alumina (90×6 cm) that was eluted with 1:1 methanol:water. Fractions containing pentosidine were pooled, dried and subjected to preparative HPLC analysis.

A separation step was achieved using reverse phase $C_{18}$ preparative column with water/acetonitrile solvent system and trifluoroacetic acid as counter-ion. Final purification was achieved with repetitive injections onto analytical $C_{18}$ reverse phase column using the same solvents as those for preparative HPLC.

A summary of the pentosidine yields produced by the comparative study using equimolar concentrations of reactants at 65° C. and 48 hours at different pH levels is set forth below in Table IV.

TABLE IV

Summary of pentosidine yields at plateau levels using equimolar concentrations of reactants at 65° C. and 48 hrs

| Reactants | pH | Yield % |
|---|---|---|
| Ribated Lysine & Arginine | 9 | 12.4 |
|  | 7.4 | 2.42 |
|  | 4 | 0.01 |
| D-Ribose, Lysine & Arginine | 9 | 3.9 |
|  | 7.4 | 2.75 |
|  | 4 | .005 |
| Glucated Lysine & Arginine | 7.4 | .99 |
| D-Glucose, Lysine & Arginine | 9 | .41 |
|  | 7.4 | .25 |
|  | 4 | 0 |
| D-Fructose, Lysine & Arginine | 7.4 | .29 |
| 3-DP, Lysine & Arginine | 9 | .139 |
|  | 7.4 | .033 |
|  | 4 | .014 |
| Ascorbate, Lysine & Arginine | 7.4 | .08 |
| Dehydroascorbate, Lysine & Arginine | 7.4 | .079 |

Figure 9A:
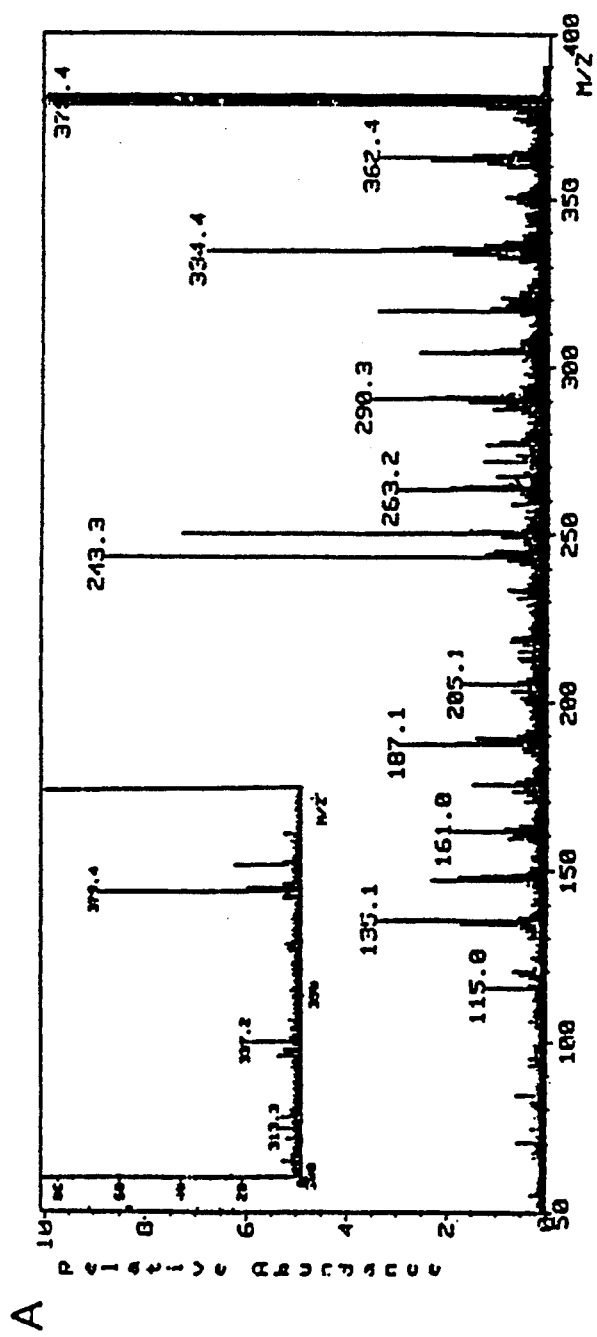
FIGS. 9A and 9B are graphs showing a comparison of the Fast Atom Bombardment Mass spectra of pentosidine produced according to the improved synthesis process of the invention from Boc-lysine Amadori products of D-ribose (FIG. 9A) and D-glucose (FIG. 9B) reacted with equimolar concentrations of Boc-arginine at 65° C. for 48 hours.
Figure 9B:
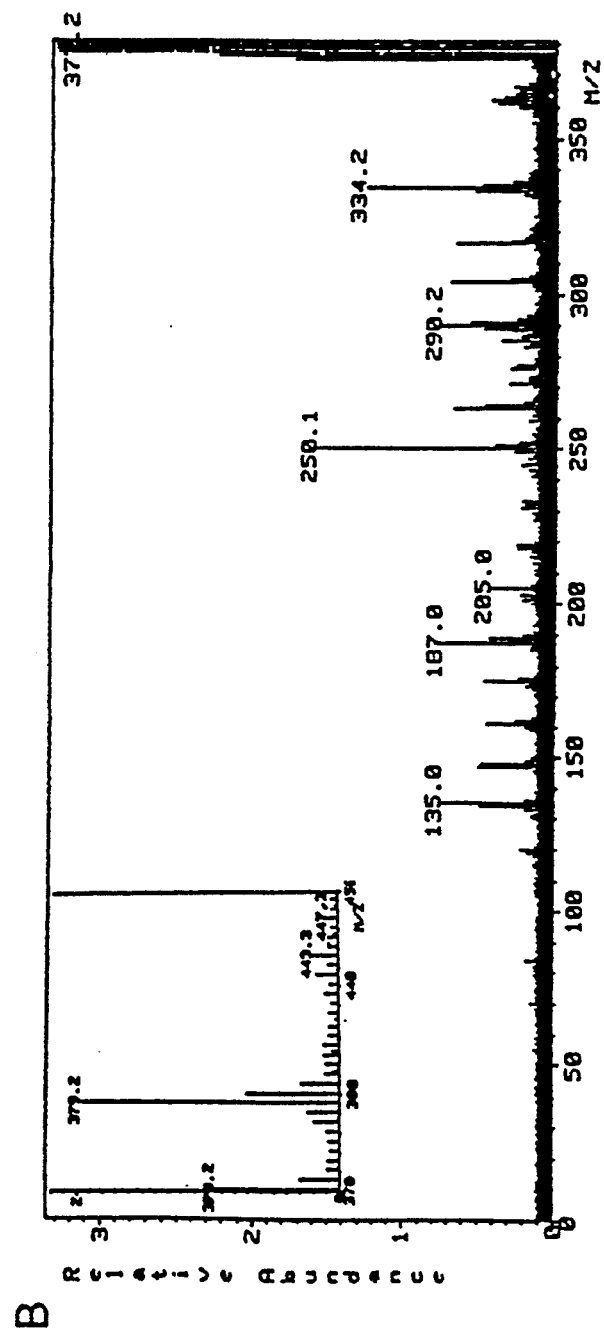
Figures 10A, 10B:
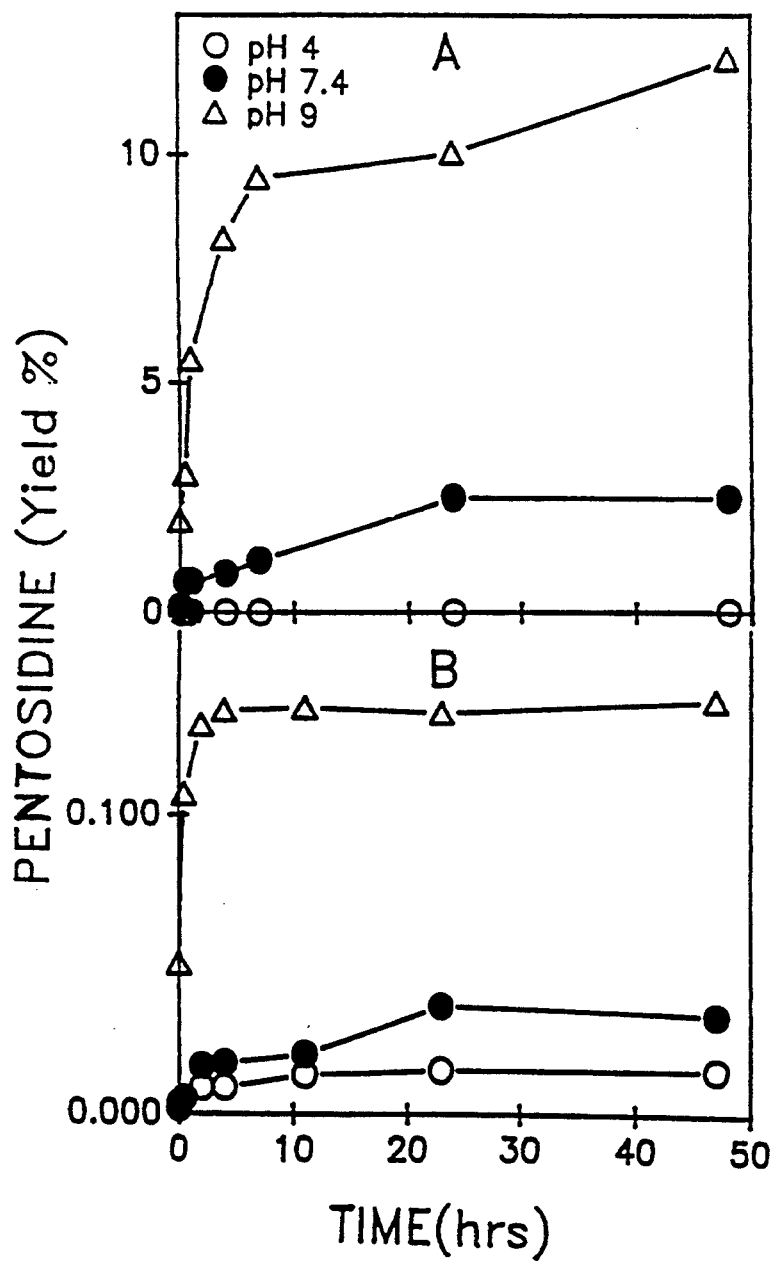
FIGS. 10A and 10B are graphs indicating the comparative rates of pentosidine from Ribated lysine with Boc-arginine (FIG. 10A) and from 3-deoxypentosone with equimolar concentrations of Boc-arginine and Boc-lysine (FIG. 10B), at various pH's of 4.0, 7.4 and 9.0.

In addition, the mass spectra of pentosidine obtained from Boc-Lysine Amadori products of D-ribose (upper) and D-glucose (lower) reacted with equimolar concentrations of Boc-arginine at 65° C. for 48 hours as set forth in FIGS. 9A and 9B. In FIGS. 10A and 10B the comparative rates of the formation of pentosidine from ribated-lysine with Boc-arginine (FIG. 10A) and from 3-deoxypent-osone reacted with equimolar concentrations of Boc-arginine and Boc-lysine (FIG. 10B), at various pH's of 4.0, 7.4 and 9.0 is shown. Similarly, comparative rates of the formation of pentosidine from D-ribose and D-glucose incubated with Boc-lysine and Boc-arginine, ribated lysine (Rib-Ama) and glucated lysine (Glu-Ama) with equimolar concentration of Boc-arginine at pH 7.4 and 65° C. demonstrated in FIG. 11.

Results and Discussion

Role of the Amadori Product in the Formation of Pentosidine

Ribated lysine (0.1M) incubated with Boc-arginine (0.1M) at 65° C., pH 7.4, for 48 hours led to the formation of a fluorescent HPLC peak which upon removal of the Boc-group with trifluoroacetic acid had the same retention time a that of pentosidine, while no such peak was observed in incubation mixtures of ribated lysine alone. The identity of the fluorophore with pentosidine was confirmed by purifying the compound from large scale incubation mixtures of ribated lysine and Boc-arginine using a combination of ion-exchange chromatography arid reverse-phase HPLC. The purified fluorescent compound was identical with original pentosidine in terms of UV, fluorescence, and proton NMR (not shown). Its MS/MS spectrum shown in FIG. 9A was identical with pentosidine synthesized from ribose. Pentosidine formed from ribated lysine five to six time faster at pH 9 than from D-ribose (yield 12.5%) while hardly any synthesis was observed at low pH (FIG. 10A).

Figure 11:
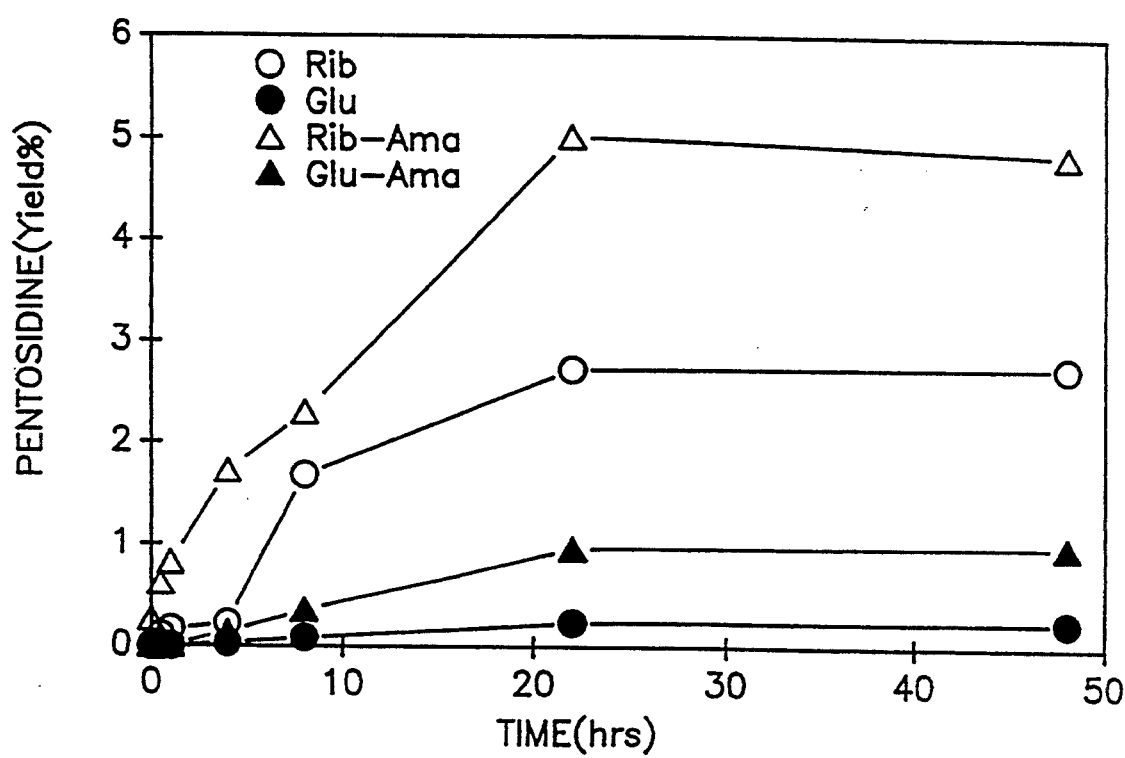
FIG. 11 is a graph showing the comparative rates of formation of pentosidine from D-ribose and D-glucose incubated with Boc-Lysine and Boc-arginine, ribated lysine (Rib-Ama) and glucated lysine (Glu-Ama) with equimolar concentration of Boc-arginine at pH 7.4° and 65° C.

Moreover, comparison of the reactivity of D-ribose, D-glucose, and their Amadori products at 65° C. showed the following reactivities: ribated lysine>ribose>glucated lysine>glucose (FIG. 11). During these experiments, it was noted that incubation mixtures of glucose/lysine as well as ribose/lysine also showed a fluorescent peak at the same retention time as pentosidine. However, the fluorophore was quenched or destroyed by borohydride treatment or HCl hydrolysis, while pentosidine derived from incubation of glucose, or ribose with lysine and arginine was stable when subjected to similar treatment.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A process for in-vitro synthesizing pentosidine comprising the steps of:
   a) providing ribated lysine; and
   b) reacting the ribated lysine with Boc-arginine at a slightly alkaline pH under bubbling with oxygen.

2. The process of claim 1, wherein the pH is about 9.

3. The process of claim 1, wherein the ribated lysine and the Boc-arginine are present in equimolar concentrations.

4. The process of claim 1, wherein the ribated lysine is synthesized from D-ribose and Boc-lysine or any lysine residue with blocked α-amino group.

5. The process of claim 1, wherein the ribated lysine is $N^\alpha$-t-Boc-$N^\alpha$-(1-deoxy-D-ribulos-1-yl)-L-lysine or any L-lysine blocked with groups other than α-Boc.

6. The process of claim 1, wherein the Boc-arginine is $N^\alpha$-t-Boc-L-arginine or any other α-amino blocked L-arginine.

7. The process of claim 1, wherein the reaction of the ribated lysine and the Boc-arginine at a slightly alkaline pH occurs at a pH of about 9 and at a temperature of about 65° C. for about 48 hours with bubbling of oxygen.

8. The pentosidine synthesized by the process of claim 1.

9. A process for chemically synthesizing an imidazo [4, 5b] pyridinium compound having a lysine and a arginine residue crosslinked by a pentose comprising the steps of:
   a) reacting α-amino protected-lysine with D-ribose, thereby producing ribated lysine; and
   b) reacting the ribated lysine with α-amino protected arginine at a slightly alkaline pH under oxygen, thereby producing the imidazo [4, 5b] pyridinium compound.

10. The process of claim 9, wherein the pH is about 9.

11. The process of claim 9, wherein the reacting step of the ribated lysine at a slightly alkaline pH occurs at a temperature of about 65° C. for about 48 hours under bubbling of oxygen.

12. The process of claim 9, further comprising the step of purifying the imidazo [4, 5b] pyridinium compound by HPLC using a C-18 reverse phase column and a linear gradient of acetonitrile with trifluoroacetic acid as the counterion.

13. A process of claim 1 for chemically synthesizing pentosidine comprising the steps of:
   a) refluxing a suspension of α-amino protected L-lysine and D-ribose in methanol to produce a refluxed mixture containing ribated lysine;
   b) evaporating the methanol from the refluxed mixture containing ribated lysine thereby producing a residue containing ribated lysine;
   c) dissolving the residue containing ribated lysine in water and loading the residue-water mixture into a Dowex 50×4 column (H+form) column;
   d) eluting the column with pyridine formate to remove the ribated lysine;
   e) incubating the ribate lysine with α-amino protected-arginine at a slightly alkaline pH, thereby producing pentosidine; and
   f) purifying the pentosidine by HPLC using a C-18 reverse phase column and a linear gradient of acetonitrile with trifluoroacetic acid as a counter ion.

14. The process of claim 13, wherein the pH is about 9 and oxygen is bubbled through the reaction mixture.

15. The process of claim 13, wherein the reaction of the ribated lysine and amino protected-arginine occurs at a pH of about 9 and at a temperature of about 65° C. for about 48 hours under presence of oxygen.

16. The pentosidine synthesized by the process of claim 13.

* * * * *